United States Patent
Chaieb et al.

(10) Patent No.: US 9,447,008 B2
(45) Date of Patent: Sep. 20, 2016

(54) ACETONE PRODUCTION USING SILICON NANOPARTICLES AND CATALYST COMPOSITIONS

(71) Applicant: King Abdullah University of Science and Technology, Thuwal (SA)

(72) Inventors: Sahraoui Chaieb, Thuwal (SA); Jehad El Demellawi, Thuwal (SA); Zeyad Al-Talla, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

(21) Appl. No.: 14/730,656

(22) Filed: Jun. 4, 2015

(65) Prior Publication Data
US 2015/0353458 A1     Dec. 10, 2015

Related U.S. Application Data

(60) Provisional application No. 62/009,354, filed on Jun. 9, 2014.

(51) Int. Cl.
| | | |
|---|---|---|
| *C07C 45/00* | (2006.01) | |
| *B01J 21/00* | (2006.01) | |
| *B01J 31/00* | (2006.01) | |
| *B01J 31/02* | (2006.01) | |
| *B01J 21/08* | (2006.01) | |
| *B01J 35/00* | (2006.01) | |

(52) U.S. Cl.
CPC .............. *C07C 45/002* (2013.01); *B01J 21/08* (2013.01); *B01J 31/0202* (2013.01); *B01J 35/0013* (2013.01)

(58) Field of Classification Search
CPC .... C07C 45/002; C07C 45/676; B01J 21/08; B01J 31/0202; C01B 33/02
USPC .......................................... 568/406; 423/348
See application file for complete search history.

(56) References Cited

U.S. PATENT DOCUMENTS

| | | | | |
|---|---|---|---|---|
| 6,585,947 | B1* | 7/2003 | Nayfeh .................. | B82Y 30/00 423/348 |
| 7,429,369 | B2* | 9/2008 | Nayfeh .................. | B82Y 30/00 423/348 |
| 8,795,906 | B2* | 8/2014 | Chaieb .............. | H01M 8/04186 429/401 |
| 2009/0011295 | A1* | 1/2009 | Yau ........................ | H01M 4/90 429/413 |
| 2010/0003520 | A1* | 1/2010 | Bujard .................. | C09C 1/0015 428/402 |
| 2014/0227548 | A1* | 8/2014 | Myrick .................. | C06B 45/30 428/570 |

* cited by examiner

*Primary Examiner* — Sikarl Witherspoon
(74) *Attorney, Agent, or Firm* — Thomas | Horstemeyer, LLP

(57) ABSTRACT

Embodiments of the present disclosure provide for a catalytic reaction to produce acetone, a catalyst that include a mixture of silicon particles (e.g., about 1 to 20 nm in diameter) and a solvent, and the like.

15 Claims, 3 Drawing Sheets

ACETONE PRODUCTION USING SILICON NANOPARTICLES AND CATALYST COMPOSITIONS

CROSS-REFERENCE TO RELATED APPLICATIONS

This application claims the benefit of and priority to U.S. Provisional Application Ser. No. 62/009,354, having the title "ACETONE PRODUCTION USING SILICON NANOPARTICLES," filed on Jun. 9, 2014, the disclosure of which is incorporated herein in by reference in its entirety.

BACKGROUND

Acetone $((CH_3)_2CO)$ is a colorless, mobile, flammable liquid and is the most simple ketone. Acetone is an important solvent and is used as a building block in many organic chemistry synthesis reactions, such as in the production of methyl methacrylate and bisphenol A. Early acetone synthesis was based on thermal decomposition of calcium acetate or carbohydrate fermentation of cornstarch. Technological advances led to acetone production though the dehydration of isopropyl alcohol or cumene peroxidation ("cumene process"). In the cumene process, benzene is alkylated with propylene to produce cumene, which is oxidized by air to produce phenol and acetone.

The cumene process is currently the preferred method used by the acetone industry. Indeed, nearly ninety percent of acetone produced is synthesized using the cumene process. One reason for this industry preference is the lower cost of production relative to other methods such as the dehydration of isopropyl alcohol. As previously described, the cumene process requires the use of benzene as a starting material and co-produces phenol as a byproduct.

Benzene is a toxic substance, which can impact cell function. For example, benzene can negatively affect bone marrow cells, which leads to decreased production of red blood cells and white blood cells. Indeed, substantial amounts of epidemiologic, clinical, and laboratory data link benzene to aplastic anemia, acute leukemia, and bone marrow abnormalities. Long-term exposure to benzene can negatively affect the reproductive organs and has been shown to be carcinogenic. Specific hematologic malignacies that benzene is associated with include: acute myeloid leukemia, aplastic anemia, myleodysplastic syndrome, acute lymphoblastic leukemia, and chronic myeloid leukemia. Benzene targets liver, kidney, lung, heart, and brain and can cause DNA strand brakes and chromosomal damage. Benzene exposure is linked to several birth defects such as spina bifida and anencephaly.

Phenol is also a toxic substance. Phenol and its vapors are corrosive to the eyes, skin, and respiratory tract. Repeated or prolonged skin contact with phenol can contribute to dermatitis or even second- or third-degree chemical burns. Phenol may also negatively affect the central nervous and cardiovascular system, resulting in dysrhythmia, seizures, coma, and/or death. Long-term or repeated exposure of phenol may be harmful to the liver and kidneys. Phenol toxicity may also be mediated by the formation of phenoxyl radicals.

Given the potential health effects of benzene and phenol, there exists a need for alternative acetone production methods. As such, it is an objective of the present embodiments to provide improved compositions and methods for the production of acetone.

SUMMARY

Embodiments of the present disclosure provide for a catalytic reaction to produce acetone, a catalyst that includes a mixture of silicon particles (e.g., about 1 to 20 nm in diameter) and a solvent, and the like.

An embodiment of the present disclosure includes a method of making acetone, among others, that includes: mixing silicon nanocrystals with an alcohol to form a catalytic mixture; and mixing the catalytic mixture with water, wherein the silicon nanocrystals, alcohol, and water react to form acetone.

An embodiment of the present disclosure includes a method of making acetone, among others, that includes: mixing silicon nanocrystals with an alcohol to form a catalytic mixture, wherein a concentration of the silicon nanocrystals in the alcohol is about 1.5 parts/million to about 1.6 parts/million; and mixing the catalytic mixture with water, wherein the silicon nanocrystals, alcohol, and water react to form acetone, wherein a concentration of the silicon nanocrystals in the alcohol is about 1.5 parts/million to about 1.6 parts/million, wherein benzene is not used to produce acetone and wherein phenol is not produced with the acetone.

An embodiment of the present disclosure includes a catalyst mixture, among others, that includes: silicon nanoparticles and a solvent, wherein a concentration of the silicon nanocrystals in the solvent is about 1.5 parts/million to about 1.6 parts/million.

DETAILED DESCRIPTION

Figure 1:
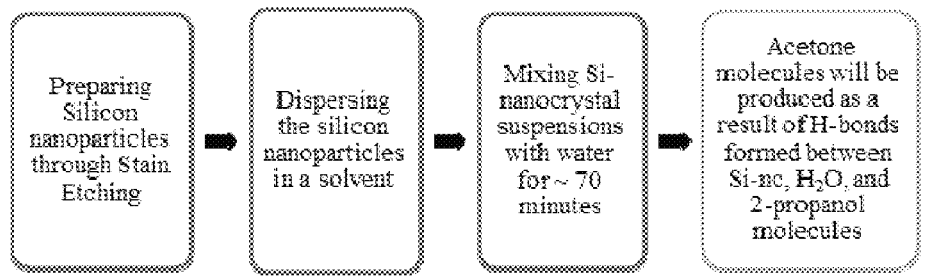
FIG. 1 shows one embodiment of a method to produce acetone using silicon nanoparticles.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, material science, and the like, which are within the skill of the art.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

DEFINITIONS

As used herein, "nanoparticle" or "nanocrystal" refers to a material that is at least one dimension smaller than 100 nm (a nanoparticle), where the size of nanocrystals distinguishes them from larger crystals. In an embodiment, silicon nanocrystals or nanoparticles refer to nanocrystals having a largest dimension (e.g., diameter) of about 1 to 50 nm or about 2-2.5 nm that are obtained by stain etching or anodic etching of doped silicon wafer.

As used herein, the phrase "green" refers to an environmentally-friendly process where the utilized nanoparticles; silicon, are biocompatible. The process does not include heavy metal nanoparticles and does not produce toxic organic byproducts.

DISCUSSION

Embodiments of the present disclosure provide for a catalytic reaction to produce acetone, a catalyst that include a mixture of silicon particles (e.g., about 1 to 20 nm in diameter) and a solvent, and the like.

The negative health effects of benzene and phenol warrant the development of improved methods of acetone production that reduce and/or eliminate the use of benzene and/or the production of phenol. One alternative to the traditional cumene process is a two-stage modified cumene process. In the first stage, a cumene hydroperoxide mixture is decomposed in the presence of a catalyst mixture to form a dicumyl peroxide mixture. The catalyst mixture from the first stage of the modified cumene process is prepared by mixing sulfuric acid and phenol in a predetermined weight ratio in a catalyst formation reactor. In the second stage, phenol and acetone are formed from decomposition of the dicumyl peroxide mixture produced in the first stage. Although this process eliminates the use of benzene, the process still co-produces phenol along with acetone. Therefore, while the hazards associated with benzene are reduced, the health risks associated with phenol remain.

Another alternative to the traditional cumene process produces acetone from acetic acid. This process is conducted at an elevated temperature of 225° C. by contacting a feed stream containing acetic acid and an optional carrier with a catalyst, such as titania, zirconia, or ceria. While problems associated with benzene and phenol are avoided, this method requires extra energy expenditure to heat the acetic acid feed-stream and utilizes transition and rare earth oxides.

Embodiments of the present disclosure include compositions and methods that do not use benzene or produce phenol to synthetically produce acetone by utilizing non-metal nanoparticles. In one embodiment, silicon nanocrystals are dispersed in an alcohol (e.g., isopropyl alcohol) to form a catalytic mixture, which is followed by mixing with water to produce acetone. Mixing the silicon nanocrystals, the alcohol, and the water produces a catalytic reaction that produces the acetone. In other words, acetone can be catalytically formed using a catalytic mixture of silicon nanocrystals and an alcohol.

At present, there is no method for producing acetone using silicon nanocrystals (e.g., nanocrystals and nanoparticles can be used interchangeably). As such, the disclosed embodiments can be employed to generate acetone in a more environmentally friendly and less hazardous way. Further, the method uses silicon nanoparticles, which are inert, biocompatible, inexpensive, and readily abundant. In addition to the benefits from not using benzene and producing phenol, one unexpected advantage of the disclosed embodiments is that they generate moles of acetone at a ratio of greater than one thousand times the number of moles of silicon nanoparticles used to in the reaction.

FIG. 1 shows one embodiment of the method of synthesizing acetone using silicon nanoparticles. Silicon nanoparticles (e.g., about 1 to 20 nm in diameter) are prepared, for example, using a stain etching method. The silicon nanoparticles are dispersed in a solvent and mixed for about 30 to 120 min or about 70 minutes. The mixture of the silicon nanoparticles and the solvent produces a catalytic mixture. The catalytic reaction generates acetone molecules that can be produced as a result of H-bonds formed between silicon nanocrystals (Si-nc), $H_2O$, and 2-propanol molecules.

Silicon nanoparticles as disclosed herein produce increased rates of acetone production compared to other available methods for synthesizing acetone. In one embodiment, the silicon nanocrystals catalyze the reaction between water and alcohol to synthesize acetone. The general reaction is shown in Scheme 1 below. The "dissociative chemisorption" of isopropanol occurs on the Si nanoparticles to produce an Si—H and an Si-isopropoxy radical. (Si—H being electron-deficient could serve as electron sinks) First isopropanol dissociated on a highly electron deficient "Si=Si" with formation of isopropoxy silicon detected by NMR and a proton detected by pH measurements. Once the isopropoxy is chemisorbed, the next step of the mechanism is the beta-H elimination with formation of acetone and silicon hydride that was detected by NMR. This silicon hydride can react with protons to give hydrogen. There would be two competitive reactions with the silicon hydride: A reaction with protons to give hydrogen or simple adsorption.

Scheme 1. The possible mechanism as probed by NMR and pH meaurements where the surface the nanoparticles is made of disilene bonds. The oxygen from Isopropoxy radical is a Hapto-2 Oxygen.

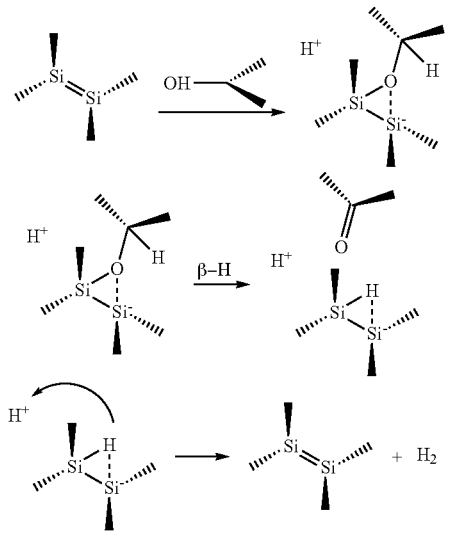

Disclosed herein are silicon nanocrystals and formulations containing silicon nanocrystals that are suitable for use in the chemical synthesis of acetone. In an embodiment, porous silicon nanocrystals are prepared through electrolytic stain etching of p-type single crystal (100-oriented) boron doped silicon wafers. In an embodiment, the silicon nanocrystals can be about 1 to 50 nm, about 1 to 20 nm, about 1 to 10 nm, about 1 to 5 nm, or about 2 to 3 nm in diameter. For some embodiments, the porous silicon nanocrystals can have a diameter of about 2 to about 2.5 nm. In further embodiments, the resistivity of the boron doped silicon wafers ranges from about 1 to about 10 Ω·cm.

The silicon wafers are then cleaved into silicon strips. For some embodiments, the silicon strips can be about 2.5 to about 4.5 cm in length. In some embodiments, the silicon strips are submerged in an etching bath. For some embodiments, the silicon strips are submerged in the etching bath for about 4 to about 5 minutes. In an embodiment, the etching bath contains an etching solution. In some embodiments, the etching solution is a mixture of hydrofluoric acid, nitric acid, and/or deionized water. In an embodiment, the ratio of hydrofluoric acid:nitric acid:deionized water can be about 1:3:4 to 3:5:6 or about 2:4:5 of hydrofluoric acid (49%, Fluka), nitric acid (69%, Fluka), and deionized water.

For some embodiments, the etched silicon strips are cleaned by rinsing in deionized water followed by rinsing in absolute ethanol. After rinsing in deionized water and absolute ethanol, the etched silicon strips are dried under a nitrogen stream. After drying, in some embodiments, the etched silicon strips are sonicated in a sonicating bath (e.g. VWR Ultrasonic Cleaner). In some embodiments, the etched silicon strips are sonicated for about 30 to about 40 minutes. The resulting nanocrystals (e.g., about 1 to 20 nm) are dispersed in a suitable solvent. In an embodiment, the solvent is isopropyl alcohol. In further embodiments, the nanocrystal samples are filtered through a suitable filter. For some embodiments, the filter is a nitrocellulose filter with a size cutoff of about 220 nm.

In other embodiments, the silicon nanoparticles can also be prepared using the electro-etching method.

In an embodiment, the alcohol can be isopropyl alcohol, 2-pentanol, 3-pentanol, 2-butanol, 2-propanol, 4-methyl-2-pentanol, a combination thereof, and the like. In particular, the alcohol is isopropyl alcohol. In an embodiment, the ratio of the alcohol to water can be about 1:100 to about 30:100. In other embodiments, the ratio of the alcohol to water can be about 1:100 to about 70:30.

In an embodiment, the mixture of the alcohol and silicon nanoparticles is a catalytic mixture. In an embodiment, the concentration of the silicon nanocrystals in the alcohol can be about 1.5 parts/million to about 1.6 parts/million.

EXAMPLES

Example 1

Production of Acetone Using Silicon Nanoparticles

A static headspace (SHS) method was used for the determination of acetone in water. Peak detection and identification was performed by Gas Chromatography Mass Spectrometry (GC/MS) and Gas Chromatography Flame Ionization Detector (GC/FID). The silicon Nano particles stock solution was prepared in 2-propanol. Before being injected into the SHS, different percentages of stock solution; typically from about 1 to about 30%, were spiked into water in a tight glass vial and left for about 70 minutes before being analyzed by GC/MS and GC/FID detectors. A two-way splitter was used to split the signal between a flame ionization detector and a mass spectrometry detector for peak identification, detection, and confirmation of acetone production.

Figure 2:
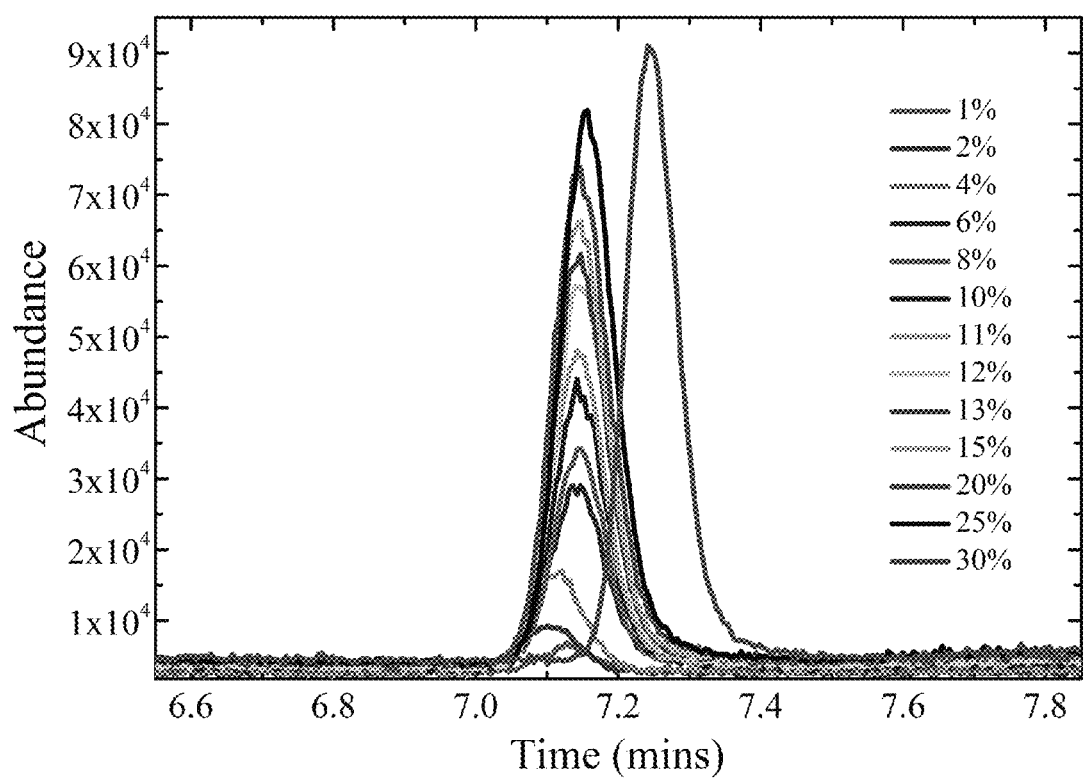
FIG. 2 demonstrates the results of a GC-MS analysis of the acetone produced according to the methods described herein.
Figure 3:
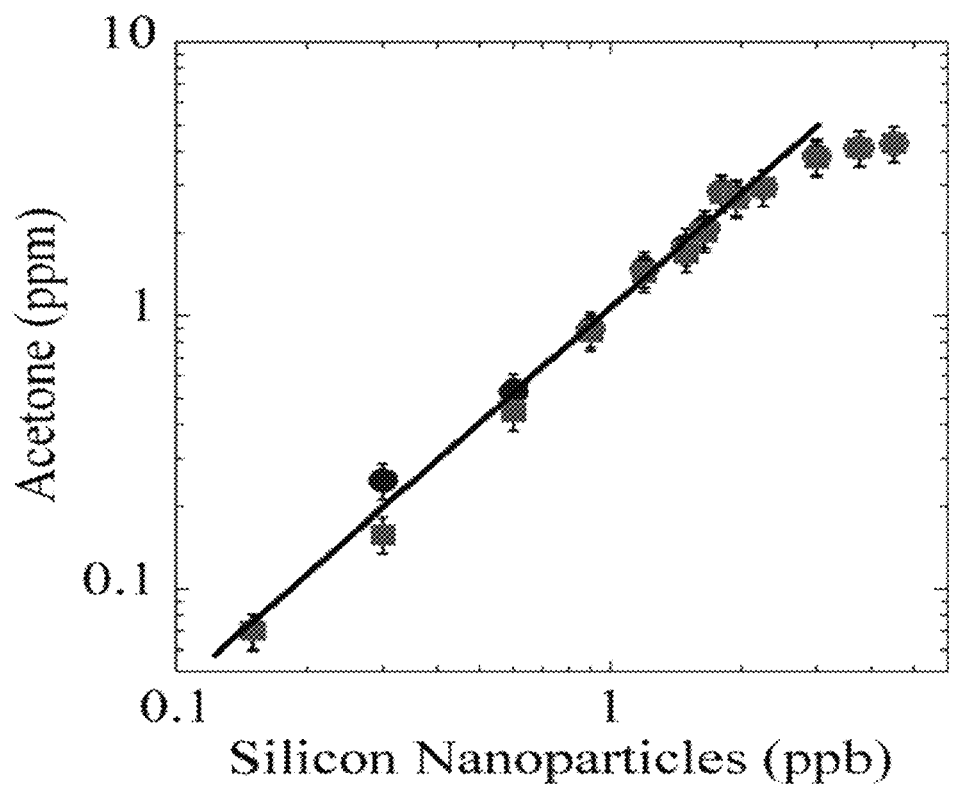
FIG. 3 is a graphical representation of the results of the GC-MS analysis of FIG. 2.
Figure 4:
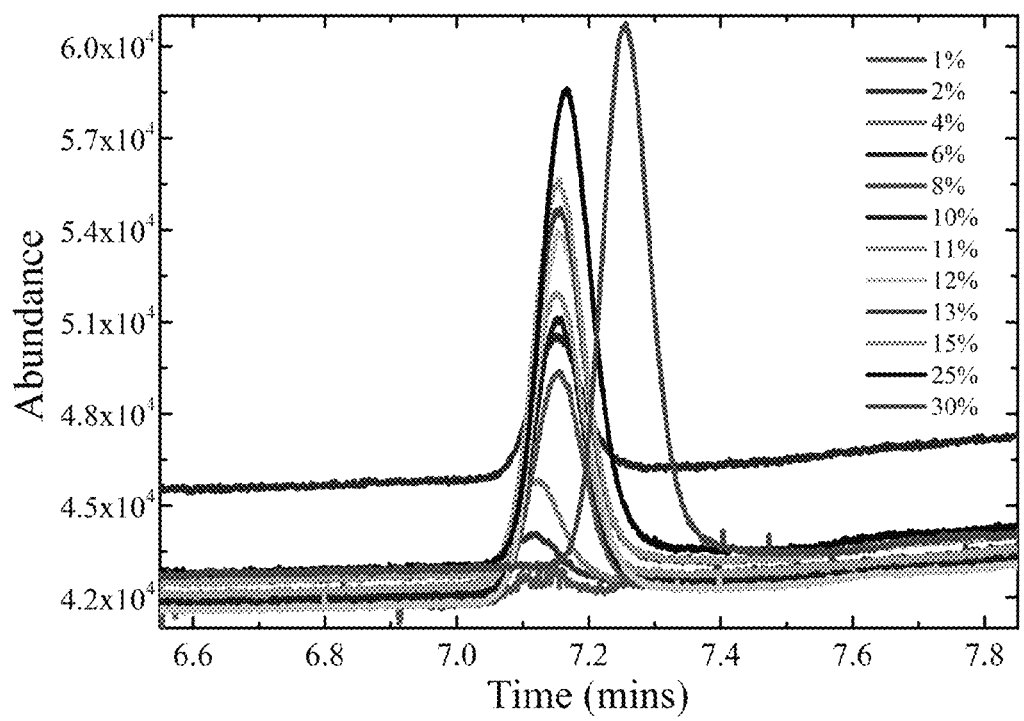
FIG. 4 demonstrates a FID analysis of acetone produced according to the methods described herein.

FIG. 2 shows the mass spectra of our solutions of silicon nanoparticles. FIG. 4 shows the flame ionization detector chromatogram of the same solutions. The results shown in FIGS. 2 and 4 demonstrate the upsurge in the production of acetone as a result of adding silicon nanoparticles.

In general, mass spectrometry (MS) detection is a well-known technique that is used to identify unknown species. It can fragment unknown analyte samples and produce a fingerprint mass spectrum. This spectrum is, then, searched against a universal built-in material database to identify the compound of interest; which is found to be acetone in this disclosure.

Flame ionization detector (FID) is a powerful instrument in measuring the concentration of organic species in a gas stream. In this embodiment, it is used to precisely quantify and confirm the acetone production.

In both MS and FID results, the peaks was acquired at the same retention time (~7.2 minutes) which is considered as an invulnerable proof of acetone production. The results shown indicate the increase in the quantity of acetone produced as a result of increasing silicon nanoparticles, where the peaks' response (abundance) is directly proportional to the amount of acetone produced.

Figure 5:
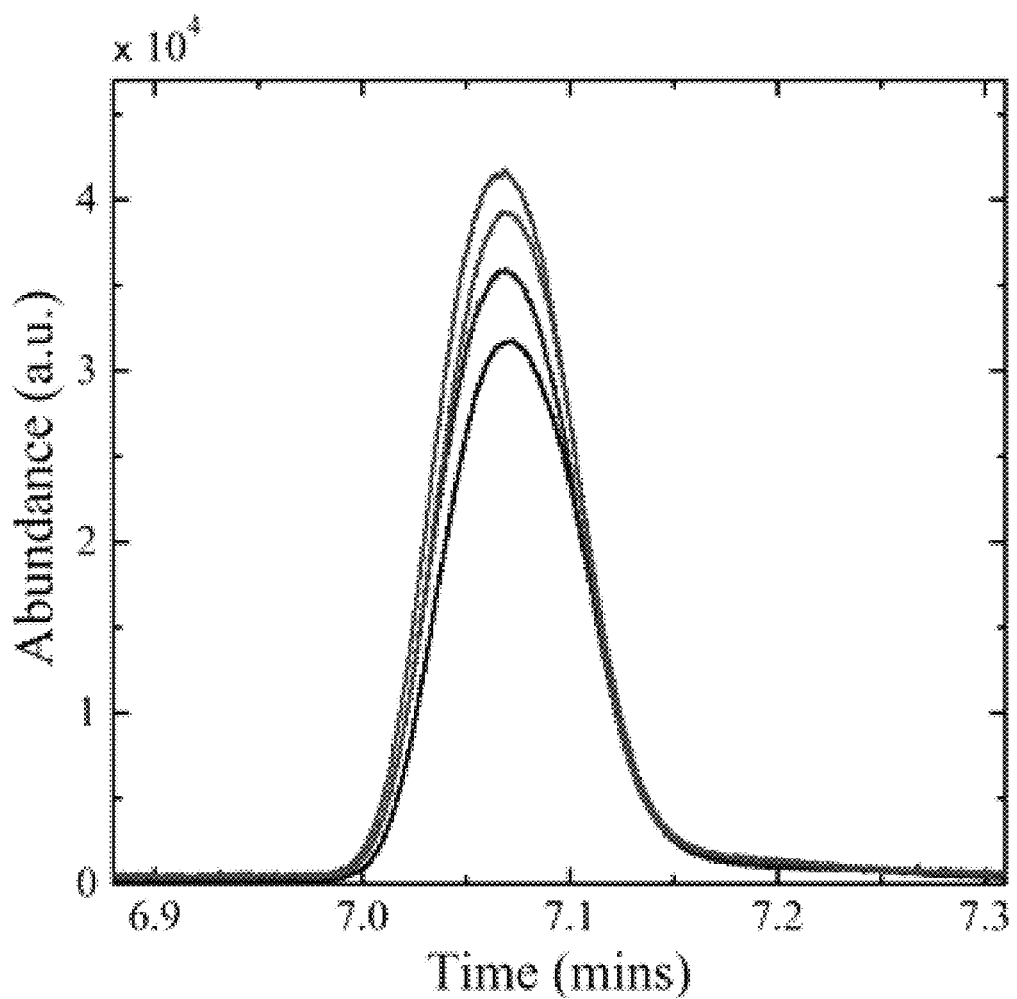
FIG. 5 illustrates a GC-FID chromatogram of 1.5 ml of SiNPs-containing IPA in 3 ml of water (black), the concentration of Si in this experiment is 1.5 µg/ml of IPA. The peak response is directly proportional to the amount of acetone produced. Notice the increase in the peak response when 1.5 ml of water is added, successively (blue (third from top), red (second from top) and green (top) spectra), to the original suspension (black spectrum). Water is added after reaching equilibrium and no more acetone is produced.

To prove that the nanoparticles are not consumed during the reaction, we measured the rate of the reaction and we found that, after equilibrium is attained, we could start a new reaction by adding more water. We noticed that more acetone is produced: The particles are recycled. We chose one ratio of water concentration to IPA containing the nanoparticles and performed GC-FID. FIG. 5 shows the renewed activity when more water is added after equilibrium is reached.

We claim:

1. A method of making acetone, comprising:
   mixing silicon nanocrystals with an alcohol to form a catalytic mixture; and
   mixing the catalytic mixture with water, wherein the silicon nanocrystals, alcohol, and water react to form acetone.

2. The method of claim 1, wherein the alcohol is selected from the group consisting of: isopropyl alcohol, 2-pentanol, 3-pentanol, 2-butanol, 2-propanol, 4-methyl-2-pentanol, and a combination thereof.

3. The method of claim 1, wherein the alcohol is isopropyl alcohol.

4. The method of claim 1, wherein benzene is not used to produce acetone.

5. The method of claim 1, wherein phenol is not produced.

6. The method of claim 1, wherein a ratio of the alcohol to water is about 1:100 to about 30:100.

7. The method of claim 1, wherein a concentration of the silicon nanocrystals in the alcohol is about 1.5 parts/million to about 1.6 parts/million.

8. The method of claim 1, wherein the silicon nanocrystals have a diameter of about 1 to 20 nm.

9. The method of claim 1, wherein the silicon nanocrystals have a diameter of about 2 to 3 nm.

10. A method of making acetone, comprising:
    mixing silicon nanocrystals with an alcohol to form a catalytic mixture, wherein a concentration of the silicon nanocrystals in the alcohol is about 1.5 parts/million to about 1.6 parts/million; and
    mixing the catalytic mixture with water, wherein the silicon nanocrystals, alcohol, and water react to form acetone, wherein a concentration of the silicon nanocrystals in the alcohol is about 1.5 parts/million to about 1.6 parts/million,
    wherein benzene is not used to produce acetone and wherein phenol is not produced with the acetone.

11. The method of claim 10, wherein the alcohol is isopropyl alcohol.

12. The method of claim 10, wherein the silicon nanocrystals have a diameter of about 2 to 3 nm.

13. A composition comprising: silicon nanoparticles and a solvent, wherein a concentration of the silicon nanocrystals in the solvent is about 1.5 parts/million to about 1.6 parts/million, wherein the solvent is selected from the group consisting of: isopropyl alcohol, 2-pentanol, 3-pentanol, 2-butanol, 2-propanol, 4-methyl-2-pentanol, and a combination thereof.

14. The composition of claim 13, wherein the silicon nanocrystals have a diameter of about 1 to 20 nm.

15. The composition of claim 13, wherein the silicon nanocrystals have a diameter of about 2 to 3 nm.

* * * * *